United States Patent [19]

Carter

[11] Patent Number: 5,599,326
[45] Date of Patent: Feb. 4, 1997

[54] CATHETER WITH MULTI-LAYER SECTION

[75] Inventor: Mark Carter, Fremont, Calif.

[73] Assignee: Target Therapeutics, Inc., Fremont, Calif.

[21] Appl. No.: 359,469

[22] Filed: Dec. 20, 1994

[51] Int. Cl.⁶ .................................................. A61M 25/00
[52] U.S. Cl. ........................................... 604/282; 604/280
[58] Field of Search .................................... 604/280–282, 604/164, 104, 105–106, 91; 606/198, 190

[56] References Cited

U.S. PATENT DOCUMENTS

| | | |
|---|---|---|
| 2,437,542 | 3/1948 | Krippendorf . |
| 3,416,531 | 12/1968 | Edwards . |
| 3,625,529 | 12/1971 | Donachy . |
| 4,196,731 | 4/1980 | Laurin et al. . |
| 4,276,874 | 7/1981 | Wolvek et al. . |
| 4,465,482 | 8/1984 | Tittel . |
| 4,484,586 | 11/1984 | McMickle et al. . |
| 4,516,972 | 5/1985 | Samson . |
| 4,569,347 | 2/1986 | Frisbie . |
| 4,636,346 | 1/1987 | Gold et al. . |
| 4,705,511 | 11/1987 | Kocak . |
| 4,739,768 | 4/1988 | Engelson . |
| 4,806,182 | 2/1989 | Rydell et al. . |
| 4,832,681 | 5/1989 | Lenck . |
| 4,840,622 | 6/1989 | Hardy . |
| 4,863,422 | 9/1989 | Stanley . |
| 4,899,787 | 2/1990 | Ouchi et al. . |
| 4,917,666 | 4/1990 | Solar et al. . |
| 4,960,410 | 10/1990 | Pinchuk . |
| 4,994,069 | 2/1991 | Ritchart et al. . |
| 5,037,404 | 8/1991 | Gold et al. . |
| 5,069,674 | 12/1991 | Fearnot et al. . |
| 5,078,702 | 1/1992 | Pomeranz . |
| 5,122,136 | 6/1992 | Guglielami et al. . |
| 5,176,660 | 1/1993 | Truckai . |
| 5,178,158 | 1/1993 | de Toledo . |
| 5,180,376 | 1/1993 | Fischell . |
| 5,211,654 | 5/1993 | Kaltenbach . |
| 5,217,482 | 6/1993 | Keith . |
| 5,226,911 | 7/1993 | Chee et al. . |
| 5,250,071 | 10/1993 | Palermo . |
| 5,261,916 | 11/1993 | Engelson . |
| 5,279,596 | 1/1994 | Castenada et al. . |
| 5,304,194 | 4/1994 | Chee et al. . |
| 5,304,195 | 4/1994 | Twyford, Jr. et al. . |
| 5,312,415 | 5/1994 | Palermo . |
| 5,344,413 | 9/1994 | Allman et al. . |
| 5,372,587 | 12/1994 | Hammerslag et al. . |

FOREIGN PATENT DOCUMENTS

| | | |
|---|---|---|
| 0596172 | 5/1994 | European Pat. Off. . |
| 0608853 | 8/1994 | European Pat. Off. . |
| 0631791 | 1/1995 | European Pat. Off. . |
| 2946385 | 5/1981 | Germany . |

Primary Examiner—Randall L. Green
Assistant Examiner—Perry E. Van Over
Attorney, Agent, or Firm—Morrison & Foerster

[57] ABSTRACT

This catheter is suitable for treating a tissue target within the body, which target is accessible through the vascular system. Central to the catheter is the use of a multi-component section having an interior stiffener comprising a spirally cut tubing member and an exterior tubing member. Depending upon the choice of materials of construction for the interior and exterior layers (and their respective thicknesses), the section may be placed at any place within the length of the catheter. The multi-component section is kink-resistant, has good pushability and flexibility, and (in some variations) has variable flexibility along the axis of the spirally cut section.

12 Claims, 2 Drawing Sheets

CATHETER WITH MULTI-LAYER SECTION

FIELD OF THE INVENTION

This invention is a surgical device. In particular, it is a catheter suitable for treating a tissue target within the body, which target is accessible through the vascular system. Central to the invention is the use of a multi-component section having an interior stiffener comprising a spirally cut tubing member and an exterior tubing member. Depending upon the choice of materials of construction for the interior and exterior layers (and their respective thicknesses), the section may be placed at any place within the length of the catheter.

BACKGROUND OF THE INVENTION

Catheters are increasingly used to access remote regions of the human body and, in doing so, delivering diagnostic or therapeutic agents to those sites. In particular, catheters which use the circulatory system as the pathway to these treatment sites are especially useful. For instance, it is commonplace to treat diseases of the circulatory system via angioplasty (PTA) using catheters having balloons on their distal tips. It is similarly common that those catheters are used to deliver a radiopaque agent to that site prior to the PTA procedure to allow viewing of the problem prior to treatment.

Often the target which one desires to access by catheter is within a soft tissue such as the liver or the brain. The difficulty in reaching such a site must be apparent even to the casual observer. The catheter must be introduced through a large artery such as those found in the groin or the neck and be passed through ever narrower regions of the arterial system until the catheter reaches a selected site. Often such pathways will wind back upon themselves in a multi-looped path. These catheters are difficult to design and use in that they must be fairly stiff at their proximal end so to allow the pushing and manipulation of the catheter as it progresses through the body, and yet must be sufficiently flexible at the distal end to allow passage of the catheter tip through the loops and increasingly smaller blood vessels mentioned above. Yet, at the same time, the catheter must not cause significant trauma to the blood vessel or other surrounding tissue. Further details on the problems and an early, but yet effective, way of designing a catheter for such a traversal may be found in U.S. Pat. No. 4,739,768, to Engelson. The Engelson catheters are designed to be used with a guidewire. A guidewire is simply a wire, typically of very sophisticated design, which is the "scout" for the catheter. The catheter fits over and slides along the guidewire as it passes through the vasculature. Said another way, the guidewire is used to select the proper path through the vasculature with the urging of the attending physician and the catheter slides along the guidewire once the proper path is established.

There are other ways of causing a catheter to proceed through the human vasculature to a selected site, but a guidewire-aided catheter is considered to be both quite quick and somewhat more accurate than the other procedures.

Once the guidewire and the catheter reach the chosen target, the guidewire is typically then removed so to allow treatment or diagnostic procedures to begin. This invention is especially suitable for placement of vasoocclusive devices. These treatment devices have been known to hang within the lumens of catheters not having special provisions to assure that those inner lumen are generally obstruction-free.

Typical of the vasoocclusive devices suitable for use with this catheter are those found in U.S. Pat. No. 4,994,069, to Ritchart et al, (vasoocclusive coils); U.S. Pat. No. 5,122,136, to Guglielmi et al (electrolytically detachable vasoocclusive coils); U.S. Pat. No. 5,226,911 and 5,304,194, to Chee et al (vasoocclusive coils with attached fibers); U.S. Pat. No. 5,250,071, to Palermo (mechanically detachable coils); U.S. Pat. No. 5,261,916, to Engelson (mechanically detachable coil); U.S. Pat. No. 5,304,195, to Twyford et al (mechanically detachable coils); and U.S. Pat. No. 5,312,415, to Palermo (mechanically detachable coils); the entirety of which are incorporated by notice. These devices each have a relatively rigid diameter and must be pushed through the lumen of the delivery catheter.

Modest kinks (or even "ovalization" of) in the smaller diameter lumens found in the distal regions of the catheter may cause major problems with delivery due either to the creation of large areas of physical interference in the lumen or simply to the contirbution of excessive sliding friction because of the distorted lumen. The creation of relatively kink-free interior regions is the goal of this invention. We have found that use of a spirally cut thin polymeric tubing in that distal region garners excellent kink resistance without raising the distal section stiffness to an unacceptable level.

Ribbons have been used in winding a catheter body to help prevent kinking. Examples of previously disclosed catheters include U.S. Pat. No. 2,437,542, to Crippendorf. Crippendorf describes a "catheter-type instrument" which is typically used as a ureteral or urethral catheter. The physical design is said to be one having a distal section of greater flexibility and a proximal section of lesser flexibility. The device is made of intertwined threads of silk, cotton, or some synthetic fiber. It is made by impregnating a fabric-based tube with a stiffening medium which renders the tube stiff yet still able to flex in the axial direction. The thus-plasticized tubing is then dipped in some other medium to allow the formation of a flexible varnish of material such as a tung oil base or a phenolic resin and a suitable plasticizer. There is no indication that this device is of the flexibility required herein. Additionally, it appears to be the type which is used in some region other than in the periphery or in soft tissues of the body.

Similarly, U.S. Pat. No. 3,416,531, to Edwards, shows a catheter having braiding-edge walls. The device further has layers of other polymers such as TEFLON and the like. The strands found in the braiding in the walls appear to be threads having classic circular cross-sections. There is no suggestion of constructing a device using a spirally cut polymer tubing. Furthermore, the device is shown to be fairly stiff in that it is designed so that it may be bent using a fairly large handle at its proximal end.

U.S. Pat. No. 4,484,586 shows a method for the production of a hollow, conductive medical tubing. The conductive wires are placed in the walls of hollow tubing specifically for implantation in the human body, particularly for pacemaker leads. The tubing is made of, preferably, an annealed copper wire which has been coated with a body-compatible polymer such as a polyurethane or a silicone. The copper wire is coated and then used in a device which winds the wire into a tube. The wound substrate is then coated with another polymer to produce a tubing having spiral conducting wires in its wall.

A document showing the use of a helically wound ribbon of flexible material in a catheter is U.S. Pat. No. 4,516,972, to Samson. This device is a guiding catheter and it may be produced from one or more wound ribbons. The preferred ribbon is an aramid material known as Kevlar 49. Again, this device is a device which must be fairly stiff. It is a device which is designed to take a "set" and remain in a particular configuration as another catheter is passed through it. It must be soft enough so as not to cause substantial trauma, but it is certainly not for use as a guidewire.

U.S. Pat. No. 4,705,511, to Kocak, shows an introducer sheath assembly having a helically spaced coil or braid placed within the wall of the device. The disclosed device is shown to be quite stiff, in that it is intended to support other catheters during their introduction in to the human body.

U.S. Pat. No. 4,806,182, to Rydell et al., shows a device using stainless steel braid imbedded in its wall and an inner layer of a polyfluorocarbon. The process also described therein is a way to laminate the polyfluorocarbon onto a polyurethane inner liner so as prevent delamination.

U.S. Pat. No. 4,832,681, to Lenck, shows a method and apparatus for artificial fertilization. The device itself is a long portion of tubing which, depending upon its specific materials of construction, may be made somewhat stiffer by the addition of spiral reinforcement comprising stainless steel wire.

Another catheter showing the use of braided wire is shown in U.S. Pat. No. 5,037,404, to Gold et al. Mention is made in Gold et al of the concept of varying the pitch angle between wound strands so to result in a device having differing flexibilities at differing portions of the device. The differing flexibilities are caused by the difference in pitch angle. No mention is made of the use of ribbon, nor is any specific mention made of the particular uses to which the Gold et al. device may be placed.

U.S. Pat. No. 5,069,674 shows a small diameter epidural catheter which is flexible and kink-resistant when flexed. The wall has a composite structure including a helical coil, typically stainless steel or the like, a tubular sheath typically of a polymer, and a safety wire which is spiraled about the coil and is often in the shape of a ribbon.

U.S. Pat. No. 5,176,660 shows the production of catheters having reinforcing strands in their sheath wall. The metallic strands are wound throughout the tubular sheath in a helical crossing pattern so to produce a substantially stronger sheath. The reinforcing filaments are used to increase the longitudinal stiffness of the catheter for good "pushability". The device appears to be quite strong and is wound at a tension of about 250,000 lb./in. or more. The flat strands themselves are said to have a width of between 0.006 and 0.020 inches and a thickness of 0.0015 and 0.004 inches.

U.S. Pat. No. 5,178,158, to de Toledo, shows a device which is a convertible wire having use either as a guidewire or as a catheter. The coil appears to be a ribbon which forms an internal passage through the coil/catheter device. No interior coating is applied.

U.S. Pat. No. 5,217,482 shows a balloon catheter having a stainless steel hypotube catheter shaft and a distal balloon. Certain sections of the device shown in the patent use a spiral ribbon of stainless steel secured to the outer sleeve by a suitable adhesive to act as a transition section from a section of very high stiffness to a section of comparatively low stiffness.

U.S. Pat. No. 5,279,596, to Castaneda et al, suggests the use of an embedded coil in the distal region of an angioplasty or angiography catheter to improve its kink-resistance. However the patent discloses neither the use of high-elasticity alloys in the coil nor does it suggest the use of the resulting catheters as the vehicles for vasoocclusive device delivery.

Similarly, multi-layer catheter sections are not, in and of themselves, unique.

U.S. Pat. No. 4,636,346, to Gold et al., shows a thin wall guiding catheter having a distal end which is adapted to be formed into a curved configuration and passed through various branching blood vessels or the like. It has a lubricious inner sheath, a rigid intermediate sheath, and a flexible outer sheath. The distal tip itself is of similar construction but the rigid intermediate sheath is sometimes omitted.

U.S. Pat. No. 4,840,622, to Hardy, shows a cannula which, again, is a multi-layer device used to direct another catheter from the exterior of a human body to some, typically, known position within the human body.

U.S. Pat. No. 4,863,442, to DeMello et al., shows a guide catheter having a tubular body with a wire-braided TEFLON core in a polyurethane jacket. The distal end of the jacket is removed form the core and a soft polyurethane tip is applied to the core over the region where the jacket has been removed. This results in a generally soft tipped but fairly stiff catheter mode up of multiple layers.

U.S. Pat. No. 5,078,702, to Pomeranz, shows a soft tip catheter, typically a guide catheter, having multiple sections of varying materials and inner and outer sheaths making up the catheter shaft. However, the intent of Pomeranz is not to produce a catheter having kink resistance, it is instead to form a soft catheter having significant stiffness. It should be noted that the material used in the inner sheath is said to be of a fairly rigid polymer (see column 4).

None of these devices are documents describe catheters having the construction described below.

SUMMARY OF THE INVENTION

This invention is a catheter section made up, desirably, of an outer tubing liner and an inner stiffener placed coaxially within that liner. The inner stiffener is a spirally cut polymeric tubing layer, typically of a material which is stiffer than the outer covering material. The outer tubing is desirably of a highly flexible material. When the section is a distal section, one or the other or both of the inner and outer layer desirably is a blend of ethylene vinyl acetate (EVA) and low density polyethylene (LDPE) or linear low density polyethylene (LLDPE). Tubing constructed of this material is highly flexible and yet has sufficient wall strength to withstand catheter pressurization without substantial radial strain. When the section is a mid or proximal section, the inner layer may be of a much stiffer material, e.g., polypropylene, polyimides, high density polyethylene (HDPE), or the like.

The catheter may be lined or coated with a hydrophilic polymer or other lubricious polymer or it may be lined with a thin layer of a lubricious polymer such as a polytetrafluoroethylene or other polyfluorocarbon.

The catheter section may be included into an integral catheter assembly. Wise choices of materials permit the catheter to be of a smaller overall diameter.

DESCRIPTION OF THE INVENTION

This invention is a kink-resistant catheter section and catheter incorporating one or more of those sections. It is a composite section including an outer covering with an inner stiffener. The inner stiffener is a helically cut polymeric tubing stiffener coaxially incorporated into that section or sections.

Figure 1:
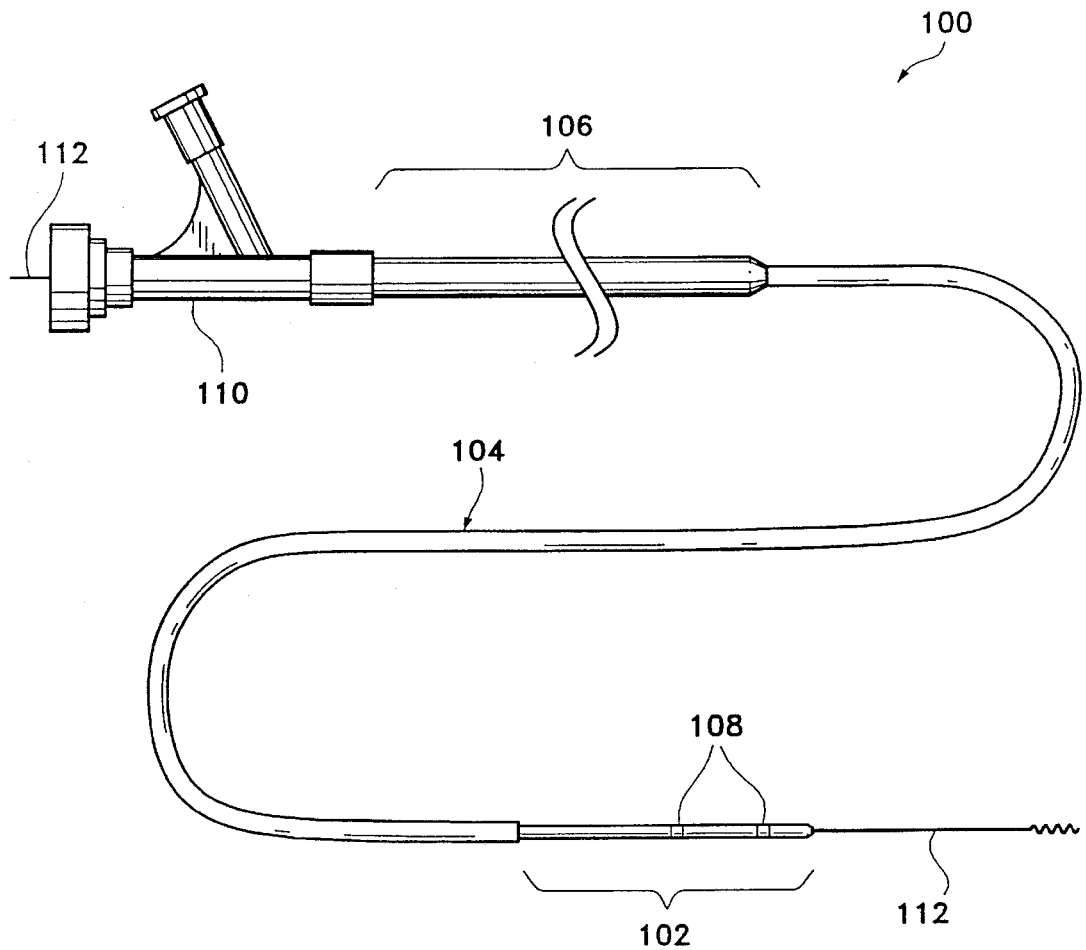
FIG. 1 shows, in side view, a typical three section catheter which may incorporate the distal section of the invention.

A typical multi-section catheter (100) which may incorporate the concepts of this invention is shown in FIG. 1. Such a catheter is described in more detail in U.S. Pat. No. 4,739,768, to Engelson, (the entirety of which is incorporated by reference) and is suitable for neurological and peripheral vascular applications. Clearly, then, it is also suitable for less demanding service such as might be encountered in access and treatment of the heart. One difficulty which has arisen as higher demands for length have been placed on these catheters is that the diameter of the distal section necessarily becomes smaller and smaller. This is so, since the longer catheters must reach ever more distal and, hence, smaller vascular areas. This smaller diameter requires a concomitant thinning of the wall section. The thinner section walls may kink or ripple when actively pushed along the guidewire or when placed in a curved vessel or when the noted vasoocclusive devices are pushed through the catheter's lumen. The typical configuration shown in FIG. 1 has a distal section (102) having significant flexibility, an intermediate section (104) which is typically less flexible, and a long proximal section (106) which in turn is least flexible. The distal section (102) is flexible and soft to allow deep penetration into the extraordinary convolutions of the neurological vasculature without trauma. Various known and necessary accessories to the catheter assembly, e.g., one or more radiopaque bands (108) at the distal region to allow viewing of the position of the distal region under fluoroscopy and a luer assembly (110) for guidewire (112) and fluids access, are also shown in FIG. 1. The typical dimensions of this catheter are:

Overall length: 60–200 cm

Proximal Section (106): 60–150 cm

Intermediate Section (104): 20–50 cm

Distal Section (102): 2.5–30 cm

Obviously, these dimensions are not particularly critical to this invention and are selected as a function of the malady treated and its site within the body.

Figure 2:
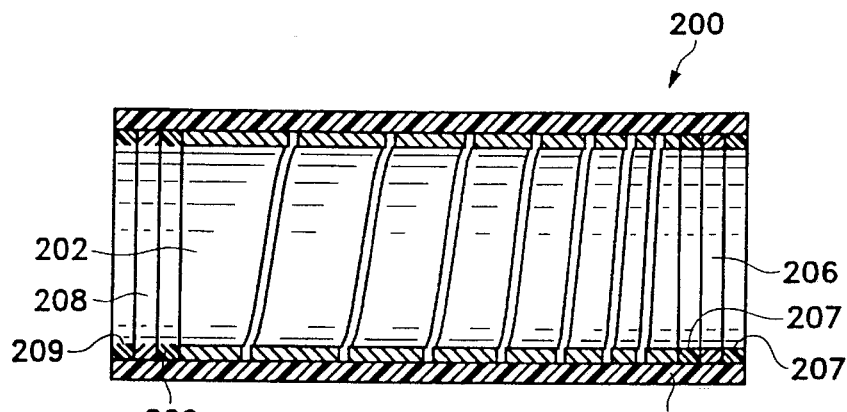
FIGS. 2, 3 and 4 show, in magnification, fragmentary cross-sections of catheter sections made according to this invention.

FIG. 2 shows a magnified section of a catheter body or section (200) showing the aspects of one variation of the invention particularly useful as the distal section of a catheter. As shown there, the catheter body or section (200) has the inner helically cut polymeric inner tubing stiffener member (202) and the outer polymeric layer (204).

The inner tubing member preferably is a simple section of tubing which has been spirally cut from its inner surface to its outer surface as shown in the drawing. The spiral cut shown in FIG. 2 is one which decreases in pitch towards the distal end to provide for a varying amount of flexibility towards the distal end of the tubing. After it has been cut, the inner section (102) is slightly stretched to provide a bit of space, e.g., 0.0005 to 0.001 inches. This allows the section to flex with more ease. The inner stiffener layer may be of a wide variety of materials but preferably is LLDPE or LDPE, perhaps containing a small amount of ethylene vinyl acetate (EVA).

The wall thickness of the tubing may be 0.005 to 0.002 inches. It is preferably about 0.0015 inches. It should be noted that the pitch of the cut in the inner layer (102) may be of any appropriate length. It may vary in pitch when a section of varying flexibility is desired. As will be shown below, the pitch may be constant if only kink resistance is desired. It should also be noted that the spiral cut need not extend from one end of the inner stiffener section to the other but only for the region in which the enhanced flexibility or kink resistance is desired.

When the section is used as a catheter distal section (or other section which requires special flexibility) the outer layer (204) may also be made of any of a wide variety of materials. These materials include polyurethanes, polyvinylchloride, LDPE, LLDPE, or mixtures of these, but preferably the outer layer (204) is a heat shrinkable tubing of LDPE or LLDPE, having an EVA content of at least 10% EVA, preferably 12 to 20% and a wall thickness of 0.005 to 0.010 inches, preferably about 0.003 inches.

These polymers may be crosslinked by radiation to increase their strength and allow heat shrinking.

Also shown in FIG. 2 is radiopaque marker (206). This distal marker (206) is made of platinum or other suitably radiopaque material so to allow the physician using the catheter to radiographically visualize the position of the catheter's distal tip when it is present in the body. An optional, proximal marker (208) is also seen in FIG. 2. The catheter section (200) shown in FIG. 2 may be made in any of a variety of ways but one acceptable way is this. The distal radiopaque marker (206) and the associated spacers are placed on a mandrel of an appropriate size adjacent the inner stiffener (202). The proximal marker (208) and adjacent spacers (209) are also placed on the mandrel. An adhesive such as thermoplastic may be applied to the outside of this assemblage but desirably is not. A heat shrinkable tubing (204) is placed over the assemblage previously placed on the interior mandrel. The tubing forming the outer layer (202) is then heat shrunk onto the assemblage. It is desirable that the material making up the inner stiffener (202) have a melt temperature in the region of that of the heat shrink temperature of the outer tubular layer (204). This creates a unitary structure having a high kink resistance in addition to the variable flexibility and pushability.

The presence of the comparatively inflexible radiopaque markers in the extremely flexible distal section of these catheters represents a challenge in producing a kink resistant device. This challenge is especially difficult when the two (or multi-) marker variation is considered. Under high flexure, the region just adjacent the markers is likely to kink and then bind upon an advancement of the relatively rigid vasoocclusive devices passed therethrough. This is especially true when the diameter of the vasoocclusive device is close in size to the inner diameter of the open lumen. We have found that the use of a single layer polymer (often a polyethylene shrinkable tubing) which is sufficiently flexible to function effectively as a distal section for tracking through the cerebral vasculature often is insufficiently strong to maintain its interior shape in the critical region near the radiopaque marker or markers. Merely increasing the thickness of the layer to alleviate the kinking problem raises the stiffness of the section to potentially unacceptable levels. By combining two layers of tubing materials as described in relationship to FIG. 2 in an overall thickness typically no greater than the thickness of the marker, the goals of enhanced kink resistance, acceptable flexibility (and trackability over a guidewire), and retention of high pushability may be met.

It should be apparent that the outer layer (204) in FIG. 2 may also be applied by dipping the inner stiffener ribbon (204) into a molten polymer bath or into a polymer dissolved in a solution or into a suspension or latex comprising the outer cover polymer. Obviously, the cover may be placed on the catheter by spraying or otherwise applying the material. Included in such a class are the polyurethanes, polysilicones, polyvinylpyrrolidone, etc.

The catheter and catheter sections of this invention may be coated or otherwise treated both inside and outside to increase their lubricity.

Figure 3:
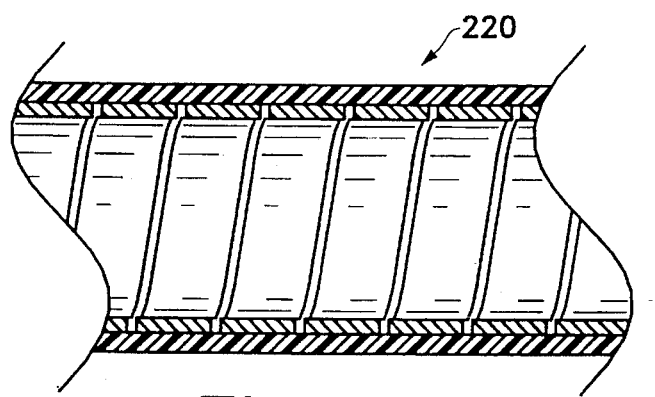

FIG. 3 shows a variation (220) of the distal section shown in FIG. 2. In this catheter section (220), the spirally cut pitch is constant but otherwise the section is identical to that earlier discussed section. This variation provides kink resistance with enhanced flexibility.

It should also be noted that each of the polymers discussed herein may be used in conjunction with radiopaque material such as barium sulfate, bismuth trioxide, bismuth carbonate, powdered tungsten, powdered tantalum, or the like so that the location of the various pieces of tubing may be radiographically visualized within the vessel. A tradeoff in decreased flexibility is typically encountered when radioopacifiers are added to the polymeric mix, however.

Figure 4:
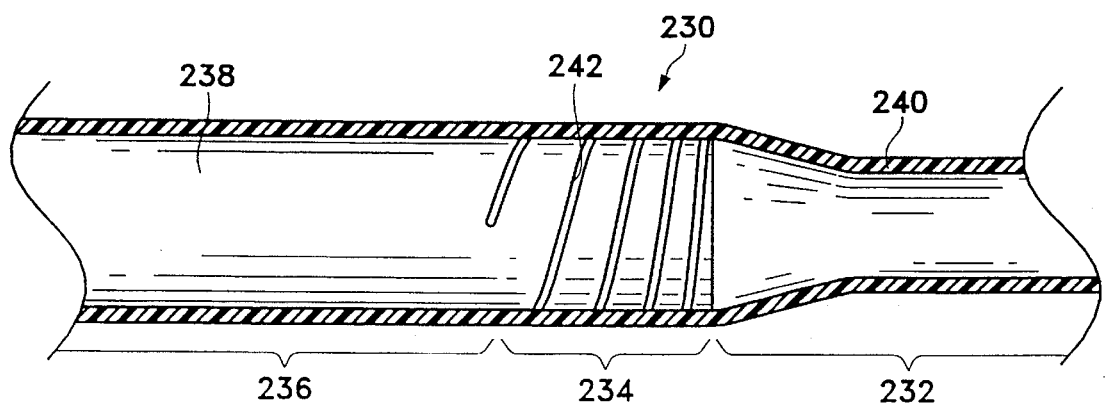

FIG. 4 shows a variation of a catheter (230) in which the spiral cut interior section is more proximal in the catheter and is not a section in which the spiral cut extends for the length of the section. The variation (230) shown in FIG. 4 is a partial cutaway view and the depicted catheter has a distal portion (232), a midportion (234) of variable flexibility, and a distal portion (236). This variation of the invention depicts a catheter which is inexpensive to manufacture and yet may incorporate all of the advantages of use described in Engelson (U.S. Pat. No. 4,738,769) above.

The physical construction of the catheter of FIG. 4 is straightforward. The depicted variation has an inner stiffener (238) made of a polymer relatively stiffer than the outer covering (240). The inner stiffener section (238) preferably is of a known polymer used in such sections such as polypropylene, high density polyethylene (HDPE), polyimides, polyamides (many of the Nylons), and some of the stiffer grades of polyethylene (LLDPE and LDPE). The spiral cut (242) extends from the outer surface of the inner stiffener section (238) to its inner surface and has preferably been slightly expanded to provide a small gap in the spiral cut. The spiral cut (242) stops at the proximal end of the mid-portion (234).

The outer covering (240) desirably is a heat-shrinkable material such as a polyethylene. Other suitable materials for this covering include polyurethane, polyvinylchloride, and other softer and compliant materials. The outer covering (240) may extend from the proximal end of the catheter to the distal end of the catheter (230).

The combination of materials shown in the FIG. 4 variation has a variety of advantages in addition to that of ease of construction. For instance, the stiff inner stiffener (238) provides an easily pushable proximal portion (238) and a transition portion (234) which retains its pushability with less stiffness than the more proximal portions and yet is significantly more flexible. The specific pattern of the spiral cut (238) in the inner stiffener (238) provides a smoother transition in stiffness between the stiffness of the proximal portion (236) and the stiffness of the distal portion (232) than does the classical choice of a section of tubing having an intermediate stiffness.

This invention has been described and specific examples of the invention have portrayed. The use of those specifics is not intended to limit the invention in any way. Additionally, to the extent that there are variations of the invention which are within the spirit of the disclosure and yet are equivalent to the inventions found in the claims, it is our intent that this patent cover those variations as well.

We claim as our invention:

1. A catheter section comprising:

an elongate tubular member having a proximal end and a distal end and a passageway defining an inner lumen extending between those ends, the elongate tubular member comprising:

a.) an inner stiffener liner of a spirally cut polymeric tubing member of a first liner material having an inner surface, an outer surface, and a longitudinal axis wherein the spiral cut extends from said inner surface to said outer surface and which inner liner is in coaxial relationship with an outer tubular cover, and b.) an outer tubular cover comprising a polymeric cover material.

2. The catheter section of claim 1 additionally comprising a distal radiopaque marker located distally of said inner stiffener liner.

3. The catheter section of claim 1 wherein the spiral cuts of the inner stiffener liner have a constant pitch.

4. The catheter section of claim 1 wherein the spiral cuts of the inner stiffener liner have a varying pitch.

5. The catheter liner of claim 1 wherein the outer cover material comprises a material selected from polyurethane, polyvinyl chloride, and polyethylene.

6. The catheter section of claim 5 wherein the outer cover material comprises a polyethylene blend containing EVA.

7. The catheter section of claim 5 wherein the inner liner material comprises a material selected from polyurethane, polyvinyl chloride, and polyethylene.

8. The catheter section of claim 7 wherein the outer cover material comprises a polyethylene blend containing EVA.

9. The catheter section of claim 1 wherein the inner liner comprises a material selected from polypropylene, polyimide, polyamide, HDPE, and polyethylene.

10. The catheter liner of claim 9 wherein the outer cover material comprises a material selected from polyurethane, polyvinyl chloride, and polyethylene.

11. The catheter section of claim 1 where the liner material and cover material are radiation sterilizable without substantial degradation of their physical attributes.

12. The catheter section of claim 1 where at least one of the liner and cover materials are radiopaque.

* * * * *

UNITED STATES PATENT AND TRADEMARK OFFICE
CERTIFICATE OF CORRECTION

PATENT NO. : 5,599,326

DATED : February 4, 1997

INVENTOR(S) : CARTER

It is certified that error appears in the above-identified patent and that said Letters Patent is hereby corrected as shown below:

Column 2, line 19, substitute --contribution-- for "contirbution".

Column 3, line 16, insert --to-- prior to "prevent".

Column 3, line 45, substitute --250,000 lb./in.$^2$-- for "250,000 lb./in".

Column 4, line 17, substitute --from-- for "form".

Column 4, line 30, insert --which-- prior to "describe".

Signed and Sealed this

Twenty-fourth Day of March, 1998

Attest:

BRUCE LEHMAN

Attesting Officer

Commissioner of Patents and Trademarks